(12) United States Patent
Sharma

(10) Patent No.: US 8,517,351 B2
(45) Date of Patent: Aug. 27, 2013

(54) CENTRIFUGAL FAN DEVICE

(75) Inventor: Nitin Sharma, Kenosha, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 386 days.

(21) Appl. No.: 13/096,527

(22) Filed: Apr. 28, 2011

(65) Prior Publication Data

US 2012/0273978 A1 Nov. 1, 2012

(51) Int. Cl.
*B01F 3/04* (2006.01)

(52) U.S. Cl.
USPC .......... 261/83; 261/94; 261/99; 261/DIG. 88; 239/44; 239/57

(58) Field of Classification Search
USPC ........ 261/83, 94, 99, 104, DIG. 88; 422/124; 239/44, 57, 58
See application file for complete search history.

(56) References Cited

U.S. PATENT DOCUMENTS

| | | |
|---|---|---|
| 3,747,902 A | 7/1973 | Bailey |
| 3,829,071 A | 8/1974 | Valbona et al. |
| 4,035,451 A | 7/1977 | Tringali |
| 4,064,203 A | 12/1977 | Cox |
| 4,166,087 A | 8/1979 | Cline et al. |
| 4,271,092 A | 6/1981 | Sullivan et al. |
| 4,383,951 A | 5/1983 | Palson |
| 4,396,557 A | 8/1983 | DeLuca |
| 4,432,938 A | 2/1984 | Meetze |
| 4,707,338 A | 11/1987 | Spector |
| 4,739,928 A | 4/1988 | O'Neil |
| 5,480,591 A | 1/1996 | Lagneaux et al. |
| 5,498,397 A | 3/1996 | Horng |
| 5,662,835 A | 9/1997 | Collingwood |
| 5,970,643 A | 10/1999 | Gawel |
| 6,050,551 A * | 4/2000 | Anderson ................ 261/30 |
| 6,371,450 B1 | 4/2002 | Davis et al. |
| 6,632,405 B2 | 10/2003 | Lua |
| 6,713,024 B1 | 3/2004 | Arnell et al. |
| 7,040,548 B2 | 5/2006 | Rodgers |
| 7,167,641 B2 | 1/2007 | Tam et al. |
| 7,175,815 B2 | 2/2007 | Yamasaki et al. |
| 7,341,698 B2 | 3/2008 | Pedrotti et al. |
| 7,382,975 B2 | 6/2008 | Caserta et al. |
| 7,499,632 B2 | 3/2009 | Granger et al. |
| 7,744,833 B2 | 6/2010 | Varanasi et al. |
| 7,748,687 B2 | 7/2010 | Pankhurst et al. |

(Continued)

FOREIGN PATENT DOCUMENTS

| | | |
|---|---|---|
| AU | 2939777 A | 4/1979 |
| EP | 0423816 A2 | 4/1991 |
| WO | 2010112895 A1 | 10/2010 |

OTHER PUBLICATIONS

PCT/US2012/035130 International Search Report dated Jul. 9, 2012.

*Primary Examiner* — Robert A Hopkins

(57) ABSTRACT

An apparatus for delivering a compound includes a reservoir containing a compound to be delivered to the environment of use. The compound includes fragrances and insecticides. A compound permeable substrate includes a wick which extends from the substrate into the reservoir. A centrifugal fan is operatively associated with the compound permeable substrate to force air over the substrate when the fan is operational. A cover is disposed over the centrifugal fan in which the cover has at least one aperture on a top surface and provides for a side air passage from the centrifugal fan to the environment.

20 Claims, 3 Drawing Sheets

(56) References Cited

U.S. PATENT DOCUMENTS

| | | |
|---|---|---|
| 7,840,123 B2 | 11/2010 | Belongia et al. |
| 7,857,236 B2 | 12/2010 | Zlotnik et al. |
| 2006/0043619 A1 | 3/2006 | Brown et al. |
| 2006/0074742 A1 | 4/2006 | Santandrea |
| 2006/0153731 A1 | 7/2006 | Brown et al. |
| 2007/0036673 A1 | 2/2007 | Selander |
| 2007/0127249 A1 | 6/2007 | Medley et al. |
| 2007/0217771 A1 | 9/2007 | Granger et al. |
| 2007/0257130 A1 | 11/2007 | Butler et al. |
| 2007/0280653 A1 | 12/2007 | Viera |
| 2008/0164337 A1 | 7/2008 | Brown et al. |
| 2008/0292508 A1 | 11/2008 | Zlotnik et al. |
| 2008/0305002 A1 | 12/2008 | Bertassi et al. |
| 2008/0311008 A1 | 12/2008 | Tranzeat |
| 2008/0315006 A1 | 12/2008 | Belongia et al. |
| 2009/0162253 A1 | 6/2009 | Porchia et al. |
| 2009/0185951 A1 | 7/2009 | Litten-Brown et al. |
| 2009/0200393 A1 | 8/2009 | Avelar |
| 2010/0044453 A1 | 2/2010 | Porchia et al. |
| 2010/0051598 A1 | 3/2010 | Butler et al. |
| 2010/0059601 A1 | 3/2010 | Bankers et al. |
| 2010/0086448 A1 | 4/2010 | Faber et al. |
| 2010/0116898 A1 | 5/2010 | Litten-Brown et al. |
| 2010/0143203 A1 | 6/2010 | Miro Amenos et al. |
| 2010/0150774 A1 | 6/2010 | Marchetti et al. |

\* cited by examiner

CENTRIFUGAL FAN DEVICE

FIELD OF THE INVENTION

The present invention is directed to a centrifugal fan device and, in particular, a centrifugal fan device which is adapted for delivering a fragrance or an insecticide to an environment during use.

BACKGROUND OF INVENTION

Many devices and apparatuses have been developed for delivering a fragrance (such as an air freshener) or insecticide (for example, citronella) to an environment of use. Some devices disseminate the fragrance or insecticide (collectively referred to as a compound) using passive means. Examples of devices with passive means include devices having a compound evaporate from a substrate or membrane which disseminate the compound into the environment. Other passive devices have a reservoir which contains a compound which is released into the environment as the compound evaporates.

In addition to the aforementioned passive devices, active devices have been developed to aid in the dissemination of the compound. Some active devices have fans which enhance the dissemination of a compound from either a substrate, membrane or reservoir. Still other devices have a heat source, separately or in combination with a fan, to disseminate the compound into the environment.

There is a need in the art for an improved apparatus for enhanced compound delivery.

SUMMARY OF THE INVENTION

The present invention is directed to a centrifugal fan device which is adapted for delivering a compound, such as a fragrance or insecticide, to an environment of use. Advantageously, the device has a reservoir for containing the compound and a compound permeable substrate. The substrate includes a series of legs or wicks which extend from a horizontal surface of the substrate to the reservoir, whereby the compound is wicked from the reservoir to the horizontal surface.

In one advantageous form, the horizontal surface of the substrate forms a top over the reservoir. In an alternative form, a cap or plug is disposed between the reservoir and the substrate, forming a cover over the reservoir. The cap or plug has holes of a sufficient size which allow the legs or wicks to extend through the holes, and into the reservoir, thereby allowing the compound to be wicked from the reservoir to the horizontal surface of the substrate.

A fan motor is disposed within a fan housing, and a centrifugal fan is connected to the motor. A cover having at least one aperture on a top surface is disposed over the centrifugal fan. The cover provides for a side passage from the centrifugal fan to the environment of use.

During operation, advantageously, the centrifugal fan draws in air from the environment of use through the aperture in the top of the cover, axially down to the centrifugal fan, radially across the compound permeable substrate, and out the side passage, back to the environment of use. In one specific embodiment, the side passage is defined by a gap formed between the cover and a base containing the reservoir.

The present invention, in one form thereof, comprises an apparatus for delivering a compound to an environment of use. The apparatus comprises a base having an exteriorly disposed reservoir defining a center cavity. The reservoir contains a compound. A compound permeable substrate has a substantially horizontal surface and at least one wick extending from the substrate into the reservoir. When a compound is disposed in the reservoir, the compound will be wicked from the reservoir onto the compound permeable substrate. A fan motor is disposed in the center cavity. A centrifugal fan is operatively associated with, and extends upward from, the fan motor. A cover is disposed over the centrifugal fan. The cover has at least one aperture through a top surface and provides a side air passage from the centrifugal fan to the environment of use.

In one embodiment, the cover comprises a plurality of apertures. In an alternative embodiment, the cover comprises a disc spaced from a main portion of the cover and is disposed over the at least one aperture. In a further specific form, the disc is attached to the main portion of the cover via a plurality of legs.

In accordance with another specific embodiment of the present invention, the base is annularly shaped, as is the reservoir defining the center cavity into which the fan housing is disposed.

The present invention, in another form thereof, is an apparatus for delivering a compound to an environment of use comprising a reservoir for containing a compound and a compound permeable substrate having a substantially horizontal surface. At least one wick extends from the substrate into the reservoir, wherein, when a compound is disposed in the reservoir, the compound will be wicked from the reservoir onto the compound permeable substrate. A centrifugal fan is at approximately a same level as a top surface of the compound permeable substrate. A cover is disposed over the centrifugal fan. The cover has at least one aperture on a top surface and provides for a side air passage from the centrifugal fan to the environment of use. During use, the centrifugal fan draws in air from the environment of use, through the aperture in the top of the cover, axially down to the centrifugal fan, radially across the compound permeable substrate, and out the side passage, back to the environment of use.

The above and other aspects of the present invention will be apparent from the following description of the preferred embodiments of the invention and from the accompanying drawings.

BRIEF DESCRIPTION OF THE DRAWINGS

The following detailed description of specific non-limiting embodiments of the present invention can be best understood when read in conjunction with the following drawings, where like structures are indicated with like reference numbers.

DETAILED DESCRIPTION OF THE PREFERRED EMBODIMENTS

Figure 1:
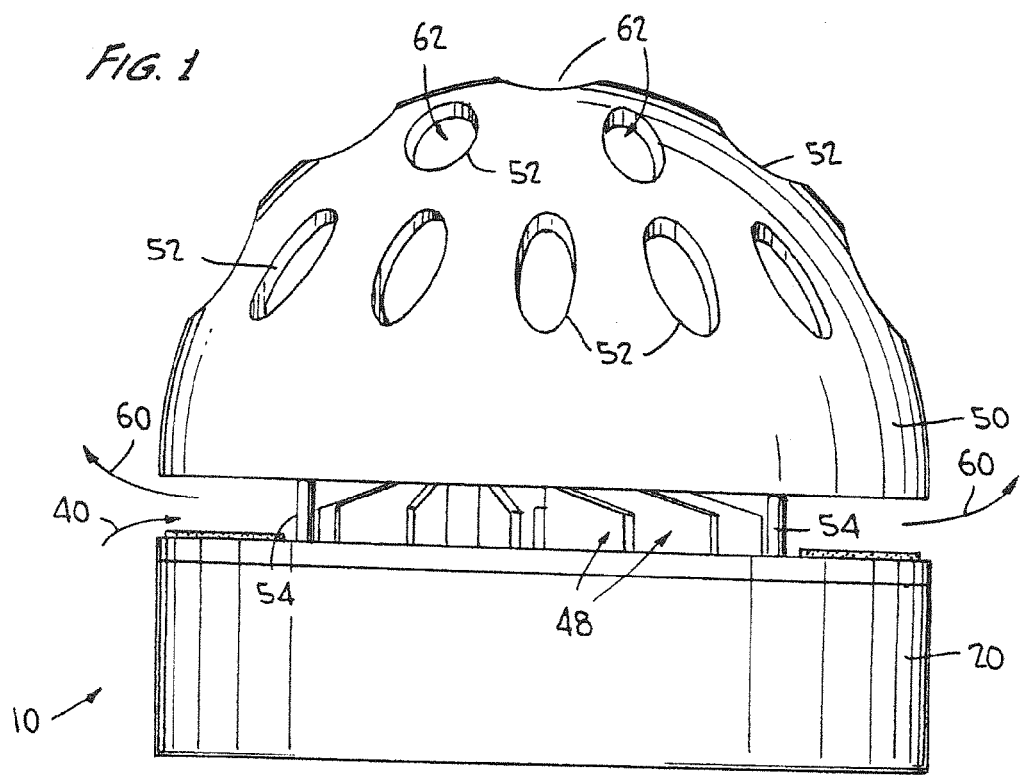
FIG. 1 is an elevational view of a centrifugal fan device, in accordance with one embodiment of the present invention.
Figure 2:
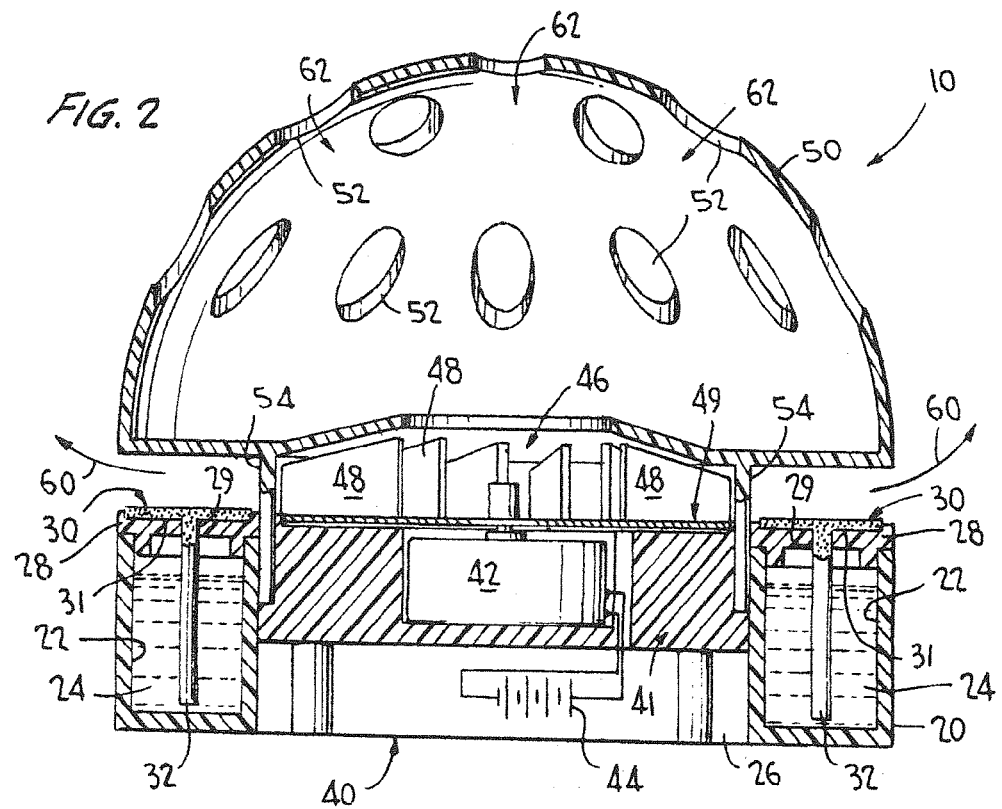
FIG. 2 is a cross-sectional view of the centrifugal fan device of FIG. 1.
Figure 3:
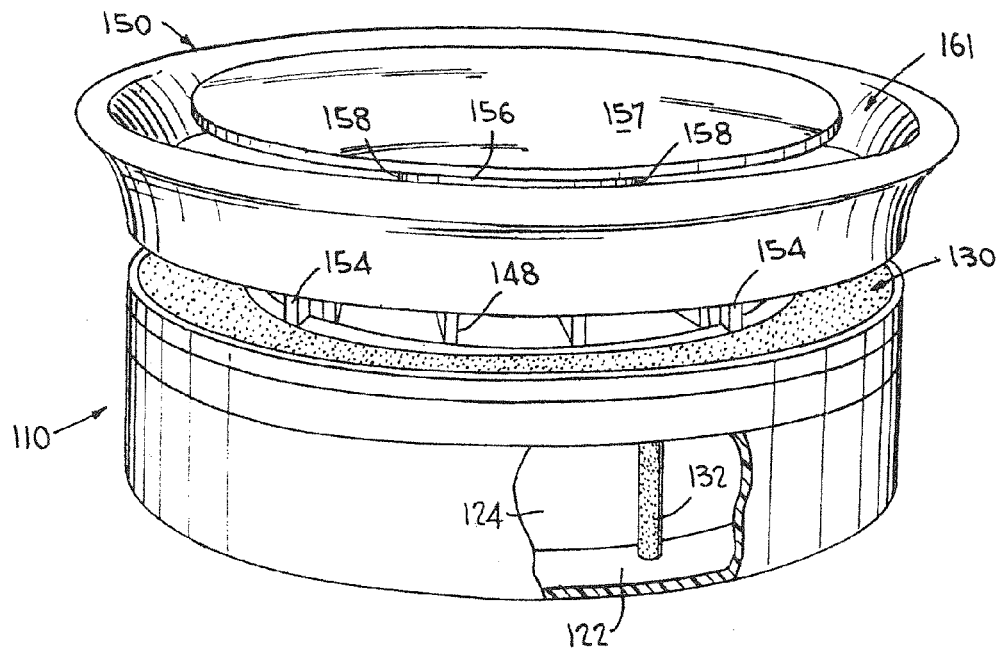
FIG. 3 is a perspective view of a centrifugal fan device, in accordance with another embodiment of the present invention, with a partial cutaway portion of a base thereof.
Figure 4:
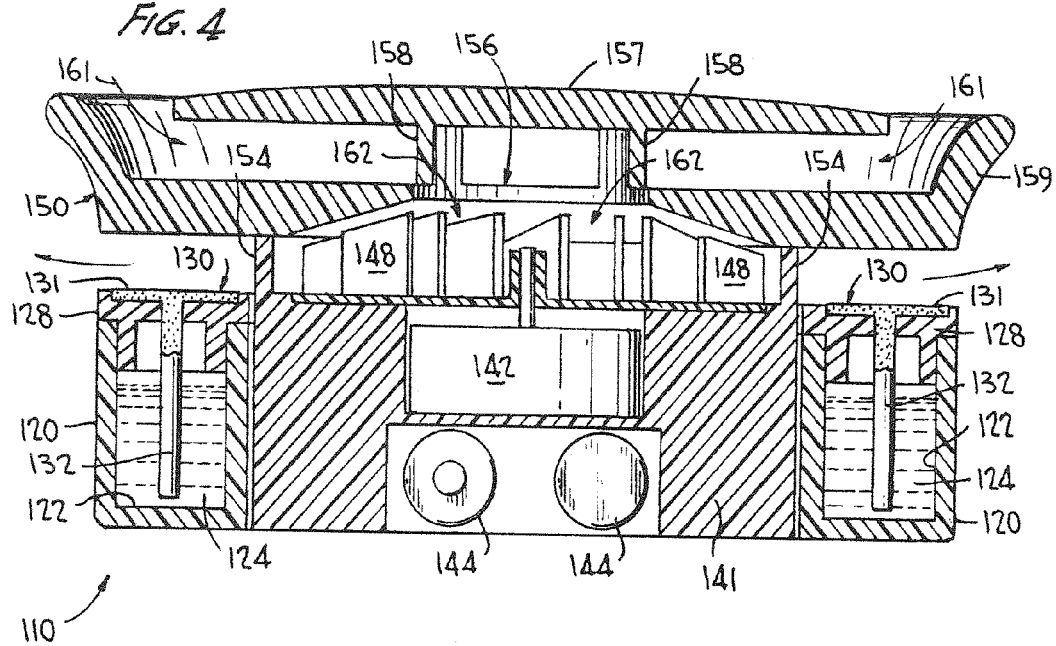
FIG. 4 is a cross-sectional view of the centrifugal fan device of FIG. 3.
Figure 5:
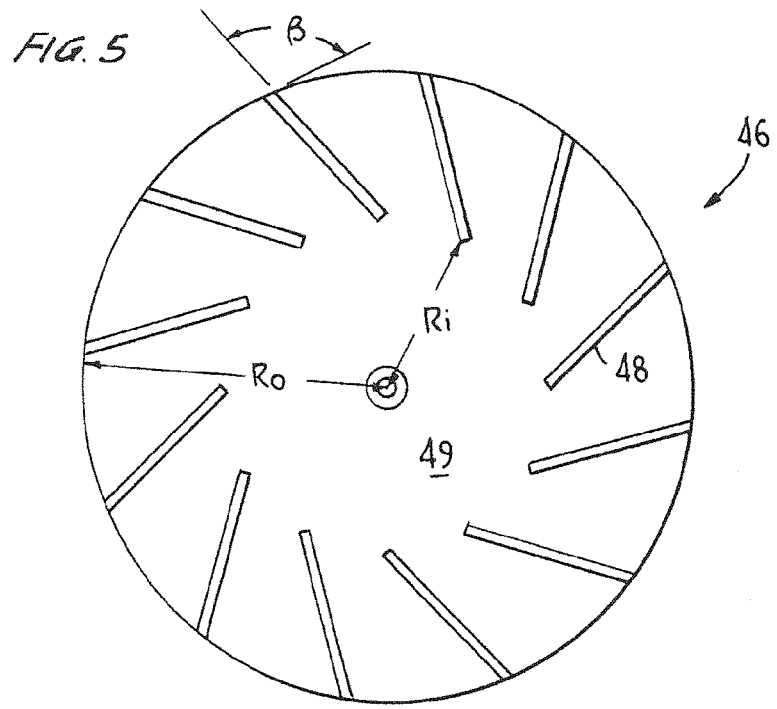
FIG. 5 is a top plan view of a centrifugal fan of the respective devices in FIGS. 1 and 3.
Figure 6:
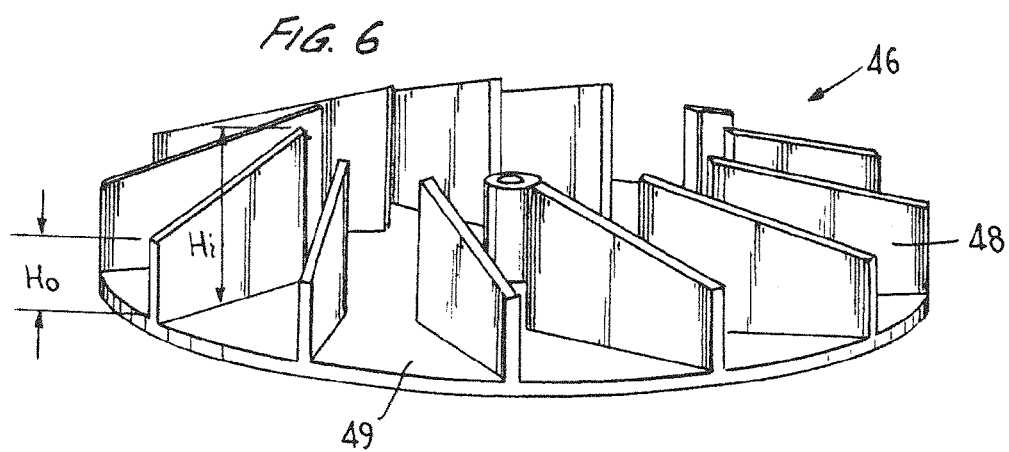
FIG. 6 is a perspective view of the centrifugal fan of FIG. 5.

The present invention will now be described with regard to FIGS. 1, 2, 5 and 6, and, in particular, FIGS. 1 and 2. Centrifugal fan device 10 includes a base 20, a compound permeable substrate 30, a fan assembly 40 and a cover 50.

The base 20 has an annularly shaped reservoir 22 into which a compound 24, such as a fragrance or insecticide, is disposed. The annularly shaped reservoir 22 defines a cylindrically shaped center cavity 26 into which the fan assembly 40 is disposed. A cap, such as plug 28, has a complementary annular shape to that of the reservoir 22, which completely covers the reservoir 22. Although the base 20 of device 10 is annularly shaped, the base can be triangular, rectangular, pentagonal, etc.

The compound permeable substrate 30 is advantageously annularly shaped, adapted to be disposed over the plug 28. A plurality of wicks 32 extend from a horizontal surface 31 into the reservoir 22 and are, thus, in contact with the compound 24. A series of bores 29 in the plug 28 are of a sufficient size to allow the wicks 32 to extend down from the horizontal surface 31, through the plug 28, to the reservoir 22 below. As a result, the compound 24 is able to be wicked from the reservoir 22 up the plurality of wicks 32 to the horizontal surface 31.

The fan assembly 40 includes a housing 41 which contains an electric motor 42 and batteries 44, although other means for powering the electric motor may be used. Further, the fan assembly 40 includes a centrifugal fan 46. The centrifugal fan 46 further comprises a plurality of fan blades 48. Advantageously, a base 49 of the centrifugal fan 46 is approximately at the same level as a horizontal surface 31 of the compound permeable substrate 30.

Advantageously, the electric motor 42 propels the centrifugal fan 46 with RPMs between 100 and 4,000 and, preferably, between 200 and 600 RPMs. Further, advantageously, the centrifugal fan 46 has between 5 and 15 blades 48 and, preferably, between 10 and 14 blades. The centrifugal fan 46 has a fan blade outlet angle ($\beta$) between 30° and 150° and, preferably, between 90° and 145°. The centrifugal fan 46 has a fan blade inner height (Hi) between 5 mm and 15 mm and, preferably, between 9 mm and 12 mm, and has a fan blade outlet height (Ho) between 20% and 100% of the fan blade inlet height and, preferably, 50% of the inlet height. The centrifugal fan 46 has a fan blade inner radius (Ri) between 5 mm and 15 mm and a fan blade outer radius (Ro) of greater than or equal to ($\geq$) 20 mm.

The cover 50 is disposed over the centrifugal fan 46. The cover comprises a plurality of apertures 52. The cover 50 provides for a side air passage from the centrifugal fan 46 to the outside environment, as identified by arrows 60. In one advantageous form, the passage is provided by a gap between the cover 50 and the base 20. The cover 50 is attached to the base 20 using a plurality of legs 54.

During use of the centrifugal fan device 10, the electric motor 42, powered by batteries 44, drives the centrifugal fan 46 to rotate, thereby drawing air in from the environment through the apertures 52 in the cover 50, as indicated by arrow 62. The air continues axially downward to the centrifugal fan 46. Then, the centrifugal fan 46 forces the air over the horizontal surface 31 of the compound permeable substrate 30 and, finally, the air exits the device 10 through the gap between the cover 50 and base 20, as identified by arrows 60.

Since the centrifugal fan 46 is substantially at the same height as a horizontal surface 31, and it directly forces air across the surface, the size of the horizontal surface 31 is minimized, as compared to the size it would have to be to achieve the same compound dispersement were the fan not at the same height as the substrate.

In addition, the centrifugal fan device 10 allows for a 360 degree dispersion of a compound 24 using the centrifugal fan 46, which draws air axially downward, in towards a center of the device, and blows air radially 360 degrees over a compound permeable substrate 30, which, as a result, becomes an evaporating surface.

Although the reservoir 22 is located below the centrifugal fan 46 in device 10, a reservoir and compound permeable substrate can be located above the centrifugal fan, e.g., in the cover section of the device.

Referring now to FIGS. 3 and 4, where like elements to those in FIGS. 1 and 2 have been increased by 100, centrifugal fan device 110 represents an alternative embodiment which is essentially the same as that of centrifugal fan device 10, except for having a different cover. Accordingly, various elements, which are the same as those in centrifugal fan device 10, are not specifically repeated here, as they are essentially the same as those in centrifugal fan device 10.

Cover 150 comprises a disc 157 which is disposed over aperture 156. A plurality of legs 158 attach the disc 157 to a main portion 159 of the cover. During use of the centrifugal fan device 110, when the centrifugal fan motor 142 is energized, thereby causing the centrifugal fan 146 to spin, air is drawn in from the environment between the disc 157 and a main portion of the cover 159, as indicated by arrow 161. Air continues through the aperture 156, as indicated by arrow 162, and is then blown radially 360 degrees over the horizontal surface 131 of the compound permeable substrate 130, which thereby acts as an evaporating surface for the compound 124.

It will now be apparent that the present centrifugal fan device provides features and advantages not found in prior devices for delivering a fragrance or insecticide. For example, the combination of the centrifugal fan 46,146, and its location adjacent the compound permeable substrate 30,130, allows for better compound delivery, as compared to other known passive and/or heated devices.

A further advantage of the present centrifugal fan device is that it allows for a small, more compact device, due to better air flow across the compound permeable substrate 30,130. As a result, the present centrifugal fan device 10,110 allows the compound permeable substrate 30,130 to have a smaller surface area and requires fewer wicks 32,132 and/or allows for a reduction in the size of wicks 32,132, as compared with prior devices, in order to achieve the same compound 24,124 delivery to the environment of use.

An additional advantage of the present centrifugal fan device is that it has less resistance to air flow, as a result of the present configuration, thus requiring a minimal amount of energy and, thus, prolonging battery life, as compared with prior devices.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. An apparatus for delivering a compound to an environment of use, said apparatus comprising:

a base having an exteriorly disposed reservoir defining a center cavity, said reservoir for containing a compound;

a compound permeable substrate having a substantially horizontal surface and at least one wick extending from the substrate into the reservoir, wherein, when a compound is disposed in the reservoir, the compound will be wicked from the reservoir onto the compound permeable substrate;

a fan motor disposed in the center cavity;

a centrifugal fan operatively associated with, and extending upward from, the fan motor; and a cover disposed over the centrifugal fan, said cover having at least one aperture on a top surface and providing a side air passage from the centrifugal fan to the environment.

2. The apparatus of claim 1, wherein the side air passage is defined by a gap formed between the cover and the base.

3. The apparatus of claim 2, wherein, when the centrifugal fan is operable, air is drawn in through the at least one aperture in the cover, passes over the substrate, and exits out the side air passage, thereby allowing for 360 degree dispersement of the compound into the environment from the apparatus.

4. The apparatus of claim 1, wherein, when the centrifugal fan is operable, air is drawn in through the at least one aperture in the cover, passes over the substrate, and exits out the side air passage.

5. The apparatus of claim 1, wherein a base of the centrifugal fan, adjacent the fan motor, is at approximately a same level as a top surface of the compound permeable substrate.

6. The apparatus of claim 1, wherein at least one wick comprises a plurality of wicks extending from the compound permeable substrate.

7. The apparatus of claim 1, wherein the at least one aperture in the cover comprises a plurality of apertures.

8. The apparatus of claim 1, wherein the compound permeable substrate is in the form of an annular disc.

9. The apparatus of claim 1, wherein the fan housing further comprises a battery for powering the fan motor.

10. The apparatus of claim 1, wherein the cover further comprises a disc spaced from a main portion of the cover and disposed over the at least one aperture.

11. The apparatus of claim 10, wherein the disc is attached to the main portion of the cover via a plurality of legs.

12. The apparatus of claim 10, wherein, when the centrifugal fan is operable, air is drawn in through the at least one aperture in the cover, passes over the substrate, and exits out the side air passage.

13. The apparatus of claim 1, wherein the reservoir is annularly shaped, defining the cylindrical center cavity.

14. The apparatus of claim 1, further comprising a fragrance disposed in the reservoir, and wherein the at least one wick is adapted to wick the fragrance from the reservoir to the compound permeable substrate.

15. The apparatus of claim 1, further comprising an insecticide disposed in the reservoir, and wherein the at least one wick is adapted to wick the insecticide from the reservoir to the compound permeable substrate.

16. The apparatus of claim 15, wherein the insecticide is citronella.

17. The apparatus of claim 1, wherein the compound permeable substrate substantially covers a top of the reservoir.

18. The apparatus of claim 1, further comprising a cap which covers a top of the reservoir, the cap being disposed between the reservoir and the compound permeable substrate.

19. The apparatus of claim 18, wherein the cap has bores through which the at least one wick is disposed, thereby allowing the compound to be drawn from the reservoir below the cap to the compound permeable substrate above the cap.

20. An apparatus for delivering a compound to an environment of use, said apparatus comprising:

a reservoir for containing a compound;

a compound permeable substrate having a substantially horizontal surface and at least one wick extending from the substrate into the reservoir, wherein, when a compound is disposed in the reservoir, the compound will be wicked from the reservoir onto the compound permeable substrate;

a centrifugal fan at approximately a same level as a top surface of the compound permeable substrate; and a cover disposed over the centrifugal fan, said cover having at least one aperture on a top surface and providing a side air passage from the centrifugal fan to the environment, wherein, during use, the centrifugal fan draws in air from the environment of use through the aperture in the top of the cover, axially down to the centrifugal fan, radially across the compound permeable substrate, and out the side passage, back to the environment of use.

* * * * *